US006764839B2

(12) United States Patent
Blakesley

(10) Patent No.: US 6,764,839 B2
(45) Date of Patent: Jul. 20, 2004

(54) METHODS FOR PREVENTING INHIBITION OF NUCLEIC ACID SYNTHESIS BY PYROPHOSPHATE

(75) Inventor: Robert W. Blakesley, Frederick, MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/883,183

(22) Filed: Jun. 19, 2001

(65) Prior Publication Data

US 2001/0055792 A1 Dec. 27, 2001

Related U.S. Application Data

(63) Continuation of application No. 08/971,675, filed on Nov. 17, 1997, now Pat. No. 6,291,164.
(60) Provisional application No. 60/031,216, filed on Nov. 22, 1996.

(51) Int. Cl.[7] .......................... C12P 19/34; C12Q 1/68; C12N 9/00
(52) U.S. Cl. ....................... 435/91.1; 435/6; 435/91.2; 435/183
(58) Field of Search ...................... 435/6, 91.1, 91.2, 435/183, 193, 195, 196; 536/23.1

(56) References Cited

U.S. PATENT DOCUMENTS

| | | |
|---|---|---|
| 4,403,035 A | 9/1983 | Anderson et al. |
| 4,595,660 A | 6/1986 | Ostroff et al. |
| 4,683,195 A | 7/1987 | Mullis et al. |
| 4,683,202 A | 7/1987 | Mullis |
| 4,766,072 A | 8/1988 | Jendrisak et al. |
| 4,767,708 A | 8/1988 | Minkley, Jr. et al. |
| 4,795,699 A | 1/1989 | Tabor et al. |
| 4,800,159 A | 1/1989 | Mullis et al. |
| 4,851,331 A | 7/1989 | Vary et al. |
| 4,863,849 A | 9/1989 | Melamede |
| 4,952,496 A | 8/1990 | Studier et al. |
| 4,962,020 A | 10/1990 | Tabor et al. |
| 4,965,188 A | 10/1990 | Mullis et al. |
| 4,971,903 A | 11/1990 | Hyman |
| 5,001,050 A | 3/1991 | Blanco et al. |
| 5,003,059 A | 3/1991 | Brennan |
| 5,026,645 A | 6/1991 | Kotani et al. |
| 5,047,342 A | 9/1991 | Chatterjee |
| 5,075,216 A | 12/1991 | Innis et al. |
| 5,079,352 A | 1/1992 | Gelfand et al. |
| 5,091,310 A | 2/1992 | Innis |
| 5,102,802 A | 4/1992 | McAllister |
| 5,106,729 A | 4/1992 | Lindsay et al. |
| 5,108,892 A | 4/1992 | Burke et al. |
| 5,122,457 A | 6/1992 | Reim et al. |
| 5,124,247 A | 6/1992 | Ansorge |
| 5,126,251 A | 6/1992 | Moss et al. |
| 5,142,033 A | 8/1992 | Innis |
| 5,173,411 A | 12/1992 | Tabor et al. |

(List continued on next page.)

FOREIGN PATENT DOCUMENTS

| | | |
|---|---|---|
| CA | 1311201 | 12/1992 |
| EP | 0 386 858 | 9/1990 |
| EP | 0 386 859 | 9/1990 |
| EP | 0 409 078 | 1/1991 |
| EP | 0 482 714 | 4/1992 |
| EP | 0 547 359 | 6/1993 |
| EP | 0 647 716 | 4/1995 |
| EP | 0 701 000 | 3/1996 |
| EP | 0 712 927 | 5/1996 |
| EP | 0 763 599 | 3/1997 |
| JP | 7-163343 | 6/1995 |
| JP | 8-9999 | 1/1996 |
| WO | WO 90/10064 | 9/1990 |
| WO | WO 90/12111 | 10/1990 |
| WO | WO 91/09950 | 7/1991 |
| WO | WO 92/06188 | 4/1992 |
| WO | WO 92/06202 | 4/1992 |
| WO | WO 93/02212 | 2/1993 |
| WO | WO 93/04184 | 3/1993 |
| WO | WO 93/05060 | 3/1993 |
| WO | WO 93/06243 | 4/1993 |
| WO | WO 93/20232 | 10/1993 |
| WO | WO 94/03643 | 2/1994 |
| WO | WO 94/05797 | 3/1994 |
| WO | WO 94/16107 | 7/1994 |

(List continued on next page.)

OTHER PUBLICATIONS

Allen, T. et al., "Cloning and expression of the adenine phosphoribosyltransferase gene from *Leishmania donovani*," *Molecular and Biochemical Parasitology 74(1)*:99–103 (Oct. 1995).

Beabealashvilli, R.S. et al., "Nucleoside 5'–triphosphates modified at sugar residues as substrates for calf thymus terminal deoxynucleotidyl transferase and for AMV reverse transcriptase," *Biochimica et Biophysica Acta 868(213)*:136–144 (1986).

(List continued on next page.)

*Primary Examiner*—Kenneth R. Horlick
*Assistant Examiner*—Young J. Kim
(74) *Attorney, Agent, or Firm*—Sterne, Kessler, Goldstein & Fox P.L.L.C.

(57) ABSTRACT

Methods for preventing inhibition of nucleic acid synthesis by pyrophosphate are disclosed. More specifically, the present invention concerns inhibiting or preventing pyrophosphorolysis in sequencing and amplification of nucleic acid molecules. According to the present invention, an enzyme which is a pentosyltransferase, a phosphotransferase with an alcohol group as acceptor, a nucleotidyltransferase, or a carboxy-lyase is added to the reaction which serves to remove pyrophosphate from the reaction mixture.

34 Claims, 3 Drawing Sheets

U.S. PATENT DOCUMENTS

| | | |
|---|---|---|
| 5,192,674 A | 3/1993 | Oshima et al. |
| 5,198,543 A | 3/1993 | Blanco et al. |
| 5,210,036 A | 5/1993 | Comb et al. |
| 5,242,818 A | 9/1993 | Oshima et al. |
| 5,270,179 A | 12/1993 | Chatterjee |
| 5,308,751 A | 5/1994 | Ohkawa et al. |
| 5,322,785 A | 6/1994 | Comb et al. |
| 5,332,666 A | 7/1994 | Prober et al. |
| 5,352,778 A | 10/1994 | Comb et al. |
| 5,374,553 A | 12/1994 | Gelfand et al. |
| 5,403,709 A | 4/1995 | Agrawal et al. |
| 5,405,746 A | 4/1995 | Uhlen |
| 5,405,747 A | 4/1995 | Jett et al. |
| 5,405,774 A | 4/1995 | Abramson et al. |
| 5,405,776 A | 4/1995 | Kotewicz et al. |
| 5,407,799 A | 4/1995 | Studier |
| 5,409,811 A | 4/1995 | Tabor et al. |
| 5,411,862 A | 5/1995 | Ruggiu et al. |
| 5,413,926 A | 5/1995 | Oshima et al. |
| 5,420,029 A | 5/1995 | Gelfand et al. |
| 5,424,190 A | 6/1995 | Fuller |
| 5,432,065 A | 7/1995 | Fuller .................. 435/91.1 |
| 5,436,149 A | 7/1995 | Barnes .................. 435/194 |
| 5,436,326 A | 7/1995 | Ishino et al. ............. 536/23.2 |
| 5,455,170 A | 10/1995 | Abramson et al. ........ 435/252.3 |
| 5,466,591 A | 11/1995 | Abramson et al. .......... 435/194 |
| 5,474,920 A | 12/1995 | Moses .................. 435/194 |
| 5,480,980 A | 1/1996 | Seela |
| 5,484,701 A | 1/1996 | Cocuzza et al. ............. 435/6 |
| 5,489,523 A | 2/1996 | Mathur .................. 435/194 |
| 5,498,523 A | 3/1996 | Tabor et al. ................ 435/6 |
| 5,500,363 A | 3/1996 | Comb et al. ............. 435/194 |
| 5,503,980 A | 4/1996 | Cantor .................... 435/6 |
| 5,512,458 A | 4/1996 | Leonard |
| 5,512,462 A | 4/1996 | Cheng |
| 5,516,633 A | 5/1996 | Fuller |
| 5,525,464 A | 6/1996 | Drmanac et al. |
| 5,525,470 A | 6/1996 | Cohen et al. |
| 5,545,552 A | 8/1996 | Mathur |
| 5,547,859 A | 8/1996 | Goodman et al. |
| 5,550,035 A | 8/1996 | Moss et al. |
| 5,665,551 A | 9/1997 | Gelfand et al. |
| 6,291,164 B1 * | 9/2001 | Blaskesley |

FOREIGN PATENT DOCUMENTS

| | | |
|---|---|---|
| WO | WO 94/26911 | 11/1994 |
| WO | WO 95/04162 | 2/1995 |
| WO | WO 95/14770 | 6/1995 |
| WO | WO 95/15380 | 6/1995 |
| WO | WO 95/20682 | 8/1995 |
| WO | WO 95/23236 | 8/1995 |
| WO | WO 95/27067 | 10/1995 |
| WO | WO 95/28636 | 10/1995 |
| WO | WO 96/10640 | 4/1996 |
| WO | WO 96/14405 | 5/1996 |
| WO | WO 96/14417 | 5/1996 |
| WO | WO 96/14434 | 5/1996 |

OTHER PUBLICATIONS

Bult, C.J. et al., "Complete Genome Sequence of the Methanogenic Archaeon, *Methanococcus jannaschii*," *Science* 273:1058–1072 (Aug. 1996).

Charng, Y. et al., "Molecular cloning and expression of the gene encoding ADP–glucose pyrophosphorylase from the cyanobacterium *Anabaena* sp. strain PCC 7120," *Plant Mol. Biol.* 20(1):37–47 (1992).

Chidgeavadze, Z.G. and R.S. Beabealashvilli, "2', 3'–Dideoxy–3'aminonucleoside 5'–triphosphates are the terminators of DNA synthesis catalyzed by DNA polymerases," *Nucl. Acids Res.* 12(3): 1671–1686 (1984).

Chidgeavadze, Z.G. et al. "3'–Fluoro–2',3'–dideoxyribonucleoside 5'–triphosphates: terminators of DNA synthesis," *FEBS Letters* 183(2):275–278 (1985).

Chidgeavadze, Z.G. et al., "Nucleoside 5'–triphosphates with modified sugars as substrates for DNA polymerases," *Biochimica et Biophysica Acta* 868(213):145–152 (1986).

Dyatkina, N. et al., "Properties of 2',3'–dideoxy–2',3'–dehydrothymidine 5'–triphosphate in terminating DNA synthesis catalyzed by several different DNA polymerases," *FEBS Letters* 219(1):151–155 (1987).

Feldmann, R.C. et al., "Decreased Metabolism and Viability of *Mycoplasma hominis* Induced by Monoclonal Antibody–Mediated Agglutination," *Infection and Immunity* 60(1):166–174 (1992).

Ghim, S. and J. Neuhard, "The Pyrimidine Biosynthesis Operon of the Thermophile *Bacillus caldolyticus* Includes Genes for Uracil Phosphoribosyltransferase and Uracil Permease," *J. Bacteriology* 176(12):3698–3707 (1994).

Hughes, K.T. et al., "The *Salmonella typhimurium nadC* Gene: Sequence Determination by Use of Mud–P22 and Purification of Quinolinate Phosphoribosyltransferase," *J. Bacteriology* 175(2): 479–486 (1993).

Jagadeeswaran, P. et al., "Nucleotide sequence and analysis of deletion mutants of the *Escherichia coli gpt* gene in plasmid pSV$_2$gpt," *Gene* 31:309–313 (1984).

Jiang, Y. et al., "*Crithidia fasciculata*:Isolation, Sequencing, and Expression of the Hypoxanthine–Guanine Phosphoribosyltransferase Gene," *Exper Parasitology* 82(1):73–75 (Jan. 1996).

Johnson, J.C. et al., "An Enzymic Method for Determination of Inorganic Pyrophosphate and Its Use as an Assay for RNA Polymerase," *Analytical Biochem.* 26(1):137–145 (1968).

Kalmar, G.B. et al., "Cloning and expression of rat liver CTP:phosphocholine cytidyltransfersase: An amphipathic protein that controls phosphatidylcholine synthesis," *Proc. Natl. Acad. Sci. USA* 87(16):6029–6033 (1990).

Kim, D. and S.M. Smith, "Molecular cloning of cucumber phosphoenolpyruvate carboxykinase and developmental regulation of gene expression," *Plant Mol. Biol.*26(1):423–434 (1994).

Kornberg, A. and T.A. Baker, "Biosynthesis of DNA Precursors," In:*DNA Replication* 2$^{nd}$ Edition,W.H. Freeman and Company publ. New York pp. 68–69 (1992).

Krayevsky, A.A. et al., "Selective Inhibition of DNA Chain Elongation Catalyzed by DNA Polymerases," *Nucleosides & Nucleotides* 7(5&6):613–617 (1988).

Kutateladze, T.V. et al., "3'–Hydroxymethyl 2'–deoxynucleoside 5'–triphosphates are inhibitors highly specific for reverse transcriptase," *FEBS Letters* 207(2):205–212 (1986).

Ladror, U.S. et al., "Cloning, Sequencing, and Expression of Pyrophosphate–dependent Phosphofructokinase from *Propionibacterium freudenreichii*," *J. Biol. Chem.* 266(25):16550–16555 (1991).

Leyh, T.S. et al., "The Sulfate Activation Locus of *Escherichia coli* K12: Cloning, Genetic, and Enzymatic Characterization," *J. Biol. Chem* 263(5): 2409–2416 (1988).

Leyh, T.S. et al., "The DNA Sequence of the Sulfate Activation Locus from *Escherichia coli* K–12," *J. Biol.Chem.* 267(15):10505–10410 (1992).

Ludin, K.M. et al., "The ade4 gene of *Schizosaccharomyces pombe*:cloning, sequence and regulation," *Curr.Genet.* 25(1):465–468 (1994).

Marolda, C.L. and M.A. Valvano, "Identification, Expression, and DNA Sequence of the GDP–Mannose Biosynthesis Genes Encoded by the 07 *rfb* Gene Cluster of Strain VW187 (*Escherichia coli* 07:K1)," *J. Bacteriology* 175(1):148–158 (1993).

Müller–Röber, B. et al., "Isolation and expression analysis of cDNA clones encoding a small and a large subunit of ADP–glucose pyrophosphorylase from sugar beet," *Plant Mol. Biol.* 27(1):191–197 (Jan. 1995).

Nakagawa, S. et al., "Nucleotide Sequence of the FAD Synthetase Gene from *Corynebacterium ammoniagenes* and Its Expression in *Escherichia coli*," *Biosci. Biotech. Biochem.* 59(4):694–702 (Apr. 1995).

Nyrén, P., "Enzymatic Method for Continuous Monitoring of DNA Polymerase Activity," *Analytical Biochem.* 167(2):235–238 (1987).

Pla, J. et al., "Cloning of the *Candida albicans* HIS1 gene by direct complementation of'a *C.albicans* histidine auxotroph using an improved double–ARS shuttle vector," *Gene* 165(1):115–120 (Nov. 1995).

Pyrinova, G.B. et al., "Selective Inhibition of Reverse Transcription in Type–A Retroviral Particles From Rat Liver by 3'–Azido–2',3'–dideoxythymidine–5'triphosphate," *Molekulyarnaya Biologiya* 22(5):1128–1132 (1988).

Rose, A.B. et al., "A Phosphoribosylanthranilate Transferase Gene Is Defective in Blue Fluorescent *Arabidopsis thaliana* Tryptophan Mutants," *Plant Physiol.* 100(2):582–592 (1992).

Ruan, C.C. et al., "Role of Pryophosphorolysis in DNA Sequencing," *Editorial Comments, US Biochemical Corp.* 17(1):1–27 (1990).

Shanmugam, K. et al., "Purification and characterization of a tRNA nucleotidyltransferase from *Lupinus albus* and functional complementation of a yeast mutation by the corresponding cDNA," *Plant Mol. Biol* 30(2):281–295 (Jan. 1996).

Siebers, B. and R. Hensel, "Glucose catabolism of the hyperthermophilic archaeum *Thermoproteus tenax*,"*FEBS Letters* 111(1):1–8 (1993).

Tabor, S. and C.C. Richardson, "DNA Sequence Analysis with a Modified Bacteriophage T7 DNA Polymerase," *J. Biol. Chem.* 256(14):8322–8328 (1990).

Vakulenko, S.B. et al., "Cloning And Nucleotide Sequence Determination of *AADB* Gene From *Salmonella oranienburg,*" *Antiobiot. Khimioter.*38(6):25–30 (1993).

Vinitsky, A. et al., "Cloning and Nucleic Acid Sequence of the *Salmonella typhimurium pnc*B Gene and Structure of Nicotinate Phosphoribosyltransferase," *J. Bacteriology* 173(2):536–540 (1991).

Vonstein, V. et al., "Molecular Cloning of the *pyrE* Gene from the Extreme Thermophile *Thermus Flavus* ," *J. Bacteriology* 177(8):4540–4543 (Aug. 1995).

Weissborn, A.C. et al., "UTP:α–D–Glucose–1–Phosphate Uridylytransferase of *Escherichia coli*:Isolation and DNA Sequence of the *galU* Gene and Purification of the Enzyme," *J. Bacteriology* 176(9):2611–2618 (1994).

Yamagishi, A. et al., "Pyrimidine Biosynthesis Gene (*pyrE* and *pyrF*) of an Extreme Thermophile, *Thermus thermophilus,*" *Applied and Environmental Microbiology* 62(6):2191–2194 (Jun. 1996).

Zapata, G. et al., "Sequence of the Cloned *Escherichia coli* K1 CMP–N–acetylneuraminic Acid Synthetase Gene," *J. Biol. Chem.* 264(25):14769–14774 (1989).

Zhu, X. et al., "Role of the Glycine 212 in the Allosteric Behavior of Phosphofructokinase from *Bacillus stearothermophilus,*" *Biochem.* 34(8):2560–2565 (Feb. 1995).

English language abstract of EP 0 409 078, WPI Accession No. 91–023706/199104.

English language abstract of EP 0 647 716, WPI Accession No. 95–140757/199519.

English language abstract of Document AS12, article by S. Vakulenko, Medline Identification No. 9421992.

Abbotts, J., et al., "Studies on the Mechanism of *Escherichia coli* DNA Polymerase I Fragment," *J. Biol. Chem.* 263:15094–15103 (1988).

Beato, M., "Gene Regulation by Steroid Hormones," *Cell* 56:335–344 (1989).

Boisclair, Y. R., and Brown, A. L., "Use of Reverse Ligation–PCR to Identify Transcriptional Start Sites in GC–Rich TATA–Less Genes: Application to the Rat IGFBP–2 Gene," *DNA and Cell Biol.* 14:731–739 (Aug. 1995).

Brock, K. V., et al., "Nucleotide sequencing of 5' and 3' termini of bovine viral diarrhea virus by RNA ligation and PCR," *J. Virol. Meth.* 38:39–46 (1992).

Brooks, R. R., and Andersen, J. A., "Substrate, Metal and Template Effects on Inhibition of Bacteriophage–Qβ Ribonucleic Acid Polymerase by Ortho– and Pyro– phosphate," *Biochem. J.* 171:725–732 (1978).

Calhoun, D. H., et al., "Location of the rho Gene and Characterization of λ ilv–gal Derivatives of λ ilv–rho Bacteriophage," *Mol. Gen. Genet.* 193:205–209 (1984).

Cunningham, P.R., and Ofengand, J., "Use of Inorganic Pyrophosphatase to Improve the Yield of *In Vitro* Transcription Reactions Catalyzed by T7 RNA Polymerase," *BioTechniques* 9:713–714 (1990).

Deissler, H., et al., "Affinity Purification and cDNA Cloning of Rat Neural Differentiation and Tumor Cell Surface Antigen gp130$^{RB13-6}$ Reveals Relationship to Human and Murine PC–1," *J. Biol. Chem.* 270:9849–9855 (Apr. 1995).

Donehower, L. A., et al., "Regulatory and Coding Potential of the Mouse Mammary Tumor Virus Long Terminal Redundancy," *J. Virol.* 37:226–238 (1981).

Elledge, S. J., et al., "λYES: A multifunctional cDNA expression vector for the isolation of genes by complementation of yeast and *Escherichia coli* mutations," *Proc. Natl. Acad. Sci. USA* 88:1731–1735 (1991).

Fisher, P. A., and Korn, D., "Ordered Sequential Mechanism of Substrate Recognition and Binding by KB Cell DNA Polymerase α," *Biochemistry* 20:4560–4569 (1981).

Fuller, C. W., et al., "Mechanism for the Initiation of Bacteriophage T7 DNA Replication," *Cold Spring Herb. Symp Quant. Biol.* 47:669–679 (1983).

Gibbs, J. S., et al., "Sequence and mapping analyses of the herpes simplex virus DNA polymerase gene predict a C–terminal substrate binding domain," *Proc. Natl. Acad. Sci. USA* 82:7969–7973 (1985).

Hörtensteiner, S., et al., "Factors affecting the re–formation of vacuoles in evacuolated protoplasts and the expression of the two vacuolar proton pumps," *Planta* 192:395–403 (1994).

Huber, H. E., et al., "*Escherichia coli* Thioredoxin Stabilizes Complexes of Bacteriophage T7 DNA Polymerase and Primed Templates," *J. Biol. Chem.* 262:16224–16232 (1987).

Hyman, E. D., "A New Method of Sequencing DNA," *Analyt. Biochem.* 174:423–436 (1988).

Kahn, J. D., and Hearst, J. E., "Reversibility of Nucleotide Incorporation by *Escherichia coli* RNA Polymerase, and Its Effect on Fidelity," *J. Mol. Biol.* 205:291–314 (1989).

Kern, D., et al., "The Glutaminyl–Transfer RNA Synthetase of *Escherichia coli*, Purification, Structure and Function Relationship," *Biochem. Biophys. Acta* 607:65–80 (1980).

Kuchta, R. D., et al., "Kinetic Mechanism of DNA Polymerase I (Klenow)," *Biochemistry* 26:8410–8417 (1987).

Kunkel, T. A. et al., "On the Fidelity of DNA Synthesis," *J. Biol. Chem.* 261:13610–13616 (1986).

Kurilova, S. A., et al., "Expression of *Saccharomyces cerevisiae* inorganic pyrophosphatase in *Escherichia coli.*," *FEBS Lett.* 333:280–282 (1993).

Lavrik, O. I., et al., "Modification of Klenow Fragment of *Escherichia coli* DNA Polymerase I at Tyrosine Residues by Acetylimidazole," *Mol. Biol.* 22:392–398 (1988).

Lecomte, P., et al., "Evidence for an Intermediate in DNA Synthesis Involving Pyrophosphate Exchange," *J. Mol. Biol.* 189:643–652 (1986).

Lee, H. Y., et al., "Cloning, Chromosomal Localization, and Tissue Expression of Autotaxin from Human Teratocarcinoma Cells," *Biochem. Biophys. Res. Comm.* 218:714–719 (Jan. 1996).

Lerchl, J., et al., "Molecular cloning, characterization and expression analysis of isoforms encoding tonoplast–bound-–proton–translocating inorganic pyrophosphatase in tobacco," *Plant Mol. Biol.* 29:833–840 (Nov. 1995).

Maruyama, K., and Sugano, S., "Oligo-capping: a simple method to replace the cap structure of eukaryotic mRNAs with oligoribonucleotides," *Gene* 138:171–174 (1994).

Matson, S. W., et al., "The Gene 4 Protein of Bacteriophage T7," *J. Biol. Chem.* 258:14017–14024 (1983).

Meyer, W., et al., "Purification, Cloning, and Sequencing of Archaebacterial Pyrophosphatase from the Extreme Thermoacidophile *Sulfolobus acidocaldarius*," *Archives Biochem. Biophys.* 319:149–156 (May 1995).

Mizrahi, V., et al., "Rate–Limiting Steps in the DNA Polymerase I Reaction Pathway," *Biochemistry* 24:4010–4018 (1985).

Mizrahi, V., et al., "Mechanism of the idling–turnover reaction of the large (Klenow) fragment of *Escherichia coli* DNA polymerase I," *Proc. Natl. Acad. Sci. USA* 83:231–235 (1986).

Möller, W., and Amons, R., "Phosphate–binding sequences in nucleotide–binding proteins," *FEBS Lett.* 186:1–7 (1985).

Murata, J., et al., "cDNA Cloning of the Human Tumor Motility–stimulating Protein, Autotaxin, Reveals a Homology with Phosphodiesterases," *J. Biol. Chem.* 269:30479–30484 (1994).

Nyrén, P., and Lundin, A., "Enzymatic Method for Continuous Monitoring of Inorganic Pyrophosphate Synthesis," *Analyt. Biochem.* 151:504–509 (1985).

Oka, M., and McCormick, D. B., "Complete Purification and General Characterization of FAD Synthetase from Rat Liver," *J. Biol Chem.* 262:7418–7422 (1987).

Papanicolaou, C., et al., "Mnemonic Aspects of *Escherichia coli* DNA Polymerase I: Interaction with One Template Influences the Next Interaction with Another Template," *J. Mol. Biol.* 189:435–448 (1986).

Peller, L., "Thermodynamic Limits on the Size and Size Distribution of Nucleic Acids Synthesized in Vitro: The Role of Pyrophosphate Hydrolysis," *Biochemistry* 16:387–395 (1977).

Putnins, R. F., and Yamada, E. W., "Calorimetric Determination of Inorganic Pyrophosphate by a Manual or Automated Method," *Analyt. Biochem.* 68:185–195 (1975).

Richter, O–M. H., and Schäfer, G., "Cloning and sequencing of the gene for the cytoplasmic inorganic pyrophosphatase from the thermoacidophilic archaebacterium *Thermoplasma acidophilum*," *Eur. J. Biochem.* 209:351–355 (1992).

Ronaghi, M., et al., "Real–Time DNA Sequencing Using Detection of Pyrophosphate Release," *Analyt. Biochem.* 242:84–89 (Nov. 1996).

Rozovskaya, T. A., et al., "Pyrophosphorolytic Reaction Catalyzed by *Escherichia coli* RNA Polymerase," *Mol. Biol.* 15:498–510 (1981).

Rubin, H., "Central role for magnesium in coordinate control of metabolism and growth in animal cells," *Proc. Natl. Acad. Sci. USA* 72:3551–3555 (1975).

Seal, G., and Loeb, L. A., "On the Fidelity of DNA Replication," *J. Biol. Chem.* 251:975–981 (1976).

Siebers, B., et al., "Ppi–Dependent Phosphofructokinase from *Thermoproteus tenax*, an Archaeal Descendent of an Ancient Line in Phosphofructokinase Evolution," *J. Bacteriol.* 180:2137–2143 (Apr. 1998).

Silverman, L. J., et al., "Genetic Analysis of Human Hypoxanthine–Guanine Phosphoribosyltransferase Deficiency," *Enzyme* 38:36–44 (1987).

Srivastava, A., and Modak, M. J., "Enzymatic Activities Associated with Avian and Murine Retroviral DNA Polymerases," *J. Biol. Chem.* 255:2000–2004 (1980).

Suttle, D. P., et al., "Molecular cloning and nucleotide sequence for the complete coding region of human UMP synthase," *Proc. Natl. Acad. Sci. USA* 85:1754–1758 (1988).

Tabor, S., and Richardson, C. C., "A bacteriophage T7 RNA polymerase/promoter system for controlled exclusive expression of specific genes," *Proc. Natl. Acad. Sci. USA* 82:1074–1078 (1985).

Tabor, S., and Richardson, C. C., "DNA sequence analysis with a modified bacteriophage T7 DNA polymerase," *Proc. Natl. Acad. Sci. USA* 84:4767–4771 (1987).

Tabor, S., and Richardson, C. C., "Selective Oxidation of the Exonuclease Domain of Bacteriophage T7 DNA Polymerase," *J. Biol. Chem.* 262:15330–15333 (1987).

Tabor, S., et al., "*Escherichia coli* Thioredoxin Confers Processivity on the DNA Polymerase Activity of the Gene 5 Protein of Bacteriophage T7," *J. Biol. Chem.* 262:16212–16223 (1987).

Tabor, S., and Richardson, C. C., "Selective Inactivation of the Exonuclease Activity of Bacteriophage T7 DNA Polymerase by in Vitro Mutagenesis," *J. Biol. Chem.* 264:6447–6458 (1989).

Tabor, S., and Richardson, C. C., "Effect of manganese ions on the incorporation of dideoxynucleotides by bacteriophage T7 DNA polymerase and *Escherichia coli* DNA polymerase I," *Proc. Natl. Acad. Sci. USA* 86:4076–4080 (1989).

Teplyakov, A., et al., "Crystal structure of inorganic pyrophosphatase from *Thermus Thermophilus,*" *Protein Science* 3:1098–1107 (1984).

English language abstract of JP 7–163343 (Document No. A08), Derwent World Patents Index, WPI Accession No. 95-260036/199534.

English language abstract of JP 8–9999 (Document No. AL9), Derwent World Patents Index, WPI Accession No. 96-110292/199612.

NCBI Entrez, Genbank Report, Accession No. D50811, Hisao, O., (May 31, 1995).

NCBI Entrez, GenBank Report, Accession No. U13860, Malone, J.A., (Aug. 19, 1994).

* cited by examiner

ACGT

METHODS FOR PREVENTING INHIBITION OF NUCLEIC ACID SYNTHESIS BY PYROPHOSPHATE

CROSS-REFERENCE TO RELATED APPLICATIONS

This application is a continuation of U.S. application Ser. No. 08/971,675, filed Nov. 17, 1997, now U.S. Pat. No. 6,291,164, which claims priority to U.S. provisional Application No. 60/031,216, filed Nov. 22, 1996, the contents of which are fully incorporated by reference herein.

BACKGROUND OF THE INVENTION

1. Field of the Invention

The present invention relates generally to methods for nucleic acid synthesis. Specifically, the present invention relates to DNA synthesis via a primer extension reaction and methods for RNA synthesis. In particular, the invention relates to methods for avoiding the inhibiting effects of pyrophosphate on RNA synthesis and primer extension DNA reactions, for example, polymerase chain reactions (PCRs) and sequencing reactions.

2. Background of the Invention

It has been recognized that pyrophosphorolysis, where an oligonucleotide is reduced in length, is detrimental to primer extension reactions. The pyrophosphorolysis is caused by the availability of pyrophosphate. For example, PCR is inhibited by the addition of pyrophosphate even at very low concentrations. According to U.S. Pat. No. 5,498,523, this pyrophosphorolysis can be prevented by providing an agent, for example, a pyrophosphatase, capable of removing pyrophosphate. Addition of pyrophosphatase to a PCR greatly enhances the progress of the reaction and provides superior results compared to the reaction without a pyrophosphatase. See U.S. Pat. No. 4,800,159. more uniformity in intensities of bands formed in a polyacrylamide gel used to identify products of the sequencing reaction. This uniformity is due to prevention of degradation of specific DNA products bypyrophosphorolysis. See also, Tabor, S. and Richardson, C. C., *J. Biol. Chem.* 265:8322 (1990); U.S. Pat. No. 4,962,020; and Ruan, C. C. et al., *Comments* 17(1):1 (1990).

Each product or band in a dideoxy sequencing experiment is a polynucleotide complementary to the template and terminated at the 3' end in a base-specific manner with a dideoxynucleotide. The dideoxy stabilizes the product, preventing further polymerization of the polynucleotide. However, in certain regions of the template, the bands, especially after prolonged reaction, will reduce in intensity or completely disappear ("drop-out" bands). A drop-out may not be readily detected by the operator, leading to errors in the interpretation of the data either by a human or computer-driven analyzer. Since this phenomenon is stimulated by inorganic pyrophosphate, the effect is presumably due to pyrophosphorolysis (reverse polymerization), not 3'-exonucleolytic activity. It is hypothesized that DNA polymerase idling at the end of these terminated products and in the presence of sufficient pyrophosphate will remove the dideoxynucleotide, then extend from the now free 3'-hydroxyl end to another dideoxy termination. In effect, the bands are converted to longer polynucleotides/bands. Removal of pyrophosphate as it is generated in the polymerization reaction eliminates this problem.

Researchers have used a series of enzyme reactions coupled to pyrophosphate generation to measure DNA polymerase activity. In the first (P. Nyren, *Anal. Biochem.* 167:235 (1987)), Nyren used ATP: sulfate adenylyltransferase to convert pyrophosphate and adenosine 5'-phosphosulfate to ATP and sulfate ion. The ATP was used to make light with luciferase. In the second (J. C. Johnson et al., *Anal. Biochem.* 26:137 (1968)), the researchers reacted the pyrophosphate with UDP-glucose in the presence of UTP: glucose-1-phosphate uridylyltransferase to produce UTP and glucose-1-phosphate. In two more steps, polymerase activity was measured spectrophotometrically by the conversion of NADP to NADPH. While these articles describe the use of ATP: sulfate adenylyltransferase and UTP: glucose-1-phosphate uridylyltransferase in measuring DNA polymerase activity, they do not describe their use to prevent or inhibit pyrophosphorolysis in nucleic acid synthesis reactions.

SUMMARY OF THE INVENTION

A number of naturally-occurring enzymes use pyrophosphate as a substrate, including certain transferases, kinases and lyases. By coupling the reaction catalyzed by one of these enzymes to the polymerase reaction, pyrophosphate will not build up, preventing pyrophosphorolysis in nucleic acid synthesis reactions. Thus, the present invention relates to a method of inhibiting or preventing pyrophosphorolysis during synthesis of a nucleic acid molecule, said method comprising (a) combining one or more nucleotides and a nucleic acid template;

(b) incubating the one or more nucleotides and nucleic acid template together with a polymerase and an enzyme selected from the group consisting of a pentosyltransferase, a phosphotransferase with alcohol group as acceptor, a nucleotidyltransferase, and a carboxy-lyase, under conditions sufficient to form a second nucleic acid molecule complementary to all or a portion of the nucleic acid template.

The method of the invention more specifically relates to a method of inhibiting or preventing pyrophosphorolysis, said method comprising (a) combining a primer with a nucleic acid template under conditions sufficient to form a hybridized product; and (b) incubating said hybridized product in the presence of (i) one or more nucleotides, (ii) a polymerase, and (iii) an enzyme selected from the group consisting of a pentosyltransferase, a phosphotransferase with alcohol group as acceptor, a nucleotidyltransferase, and a carboxy-lyase under conditions sufficient to synthesize a second nucleic acid molecule complementary to all or a portion of said nucleic acid template.

Specifically, the method of the present invention relates to inhibition of pyrophosphorolysis in the synthesis of DNA and RNA molecules using the appropriate nucleotides and polymerases (dNTP's/rNTP's and DNA polymerase/RNA polymerase).

In particular, the present invention may be used in primer extension reactions to prevent the inhibition of nucleic acid synthesis during amplification and may be used to prevent band drop out in sequencing reactions. Thus, the invention relates to a method to prevent inhibition of nucleic acid synthesis during amplification of a double stranded nucleic acid molecule comprising (a) providing a first and second primer, wherein said first primer is complementary to a sequence at or near the 3' termini of the first strand of said nucleic acid molecule and said second primer is complementary to a sequence at or near the 3' termini of the second strand of said nucleic acid molecule;

(b) hybridizing said first primer to said first strand and said second primer to said second strand in the presence of (i) a polymerase, and (ii) an enzyme selected from the group consisting of a pentosyltransferase, a phosphotransferase with an alcohol group as an acceptor, a nucleotidyltransferase and a carboxy-lyase under conditions such that a third nucleic acid molecule complementary to said first strand and a fourth nucleic acid molecule complementary to said second strand are synthesized;

(c) denaturing said first and third strand and said second and fourth strand; and (d) repeating steps (a) to (c) one or more times.

The present invention also relates to a method of sequencing a DNA molecule comprising:

(a) combining a primer with a first DNA molecule under conditions sufficient to form a hybridized product;

(b) contacting said hybridized product with nucleotides, a DNA polymerase, an enzyme selected from the group consisting of a pentosyltransferase, a phosphotransferase with an alcohol group as acceptor, a nucleotidyltransferase and a carboxy-lyase; and a terminator nucleotide to give a reaction mixture;

(c) incubating the reaction mixture under conditions sufficient to synthesize a random population of DNA molecules complementary to said first DNA molecule, wherein said synthesized DNA molecules are shorter in length than said first DNA molecule and wherein said synthesized DNA molecules comprise a terminator nucleotide at their 3' termini; and (d) separating said synthesized DNA molecules by size so that at least a part of the nucleotide sequence of said first DNA molecule can be determined.

The invention also relates to a solution for use in nucleic acid synthesis, amplification or sequencing, comprising (a) an enzyme selected from the group consisting of a pentosyltransferase, a phosphotransferase with alcohol group as acceptor, a nucleotidyltransferase, and a carboxy-lyase;

(b) a substrate which is capable of either accepting a phosphate radical from pyrophosphate or effecting transfer of pyrophosphate to give a phosphorylated product when in the presence of said enzyme; and (c) a polymerase.

Examples of pentosyltransferases according to the present invention include an adenine phosphoribosyltransferase or an orotate phosphoribosyltransferase. Examples of a phosphotransferase with alcohol group as acceptor include a pyrophosphate: glycerol phosphotransferase, a pyrophosphate: serine phosphotransferase, a pyrophosphate: fructose-6-phosphate 1-phosphotransferase or a pyrophosphate: purine nucleoside kinase. Examples of a nucleotidyltransferase include an ATP: sulfate adenylyltransferase, a UTP: glucose-1-phosphate uridylyltransferase or a glucose-1-phosphate adenylyltransferase. Examples of a carboxy-lyase include phosphoenolpyruvate carboxykinase.

The invention also relates to a kit comprising a container means having in close confinement therein two or more container means, wherein a first container means comprises an enzyme selected from the group consisting of a pentosyltransferase, a phosphotransferase with an alcohol group as acceptor, a nucleotidyltransferase, and a carboxy-lyase; and optionally a nucleic acid polymerase. The polymerase may instead be contained in a second container means. A third container means comprises a substrate which is capable of either accepting a phosphate radical to give a phosphorylated product from pyrophosphate or effecting transfer of pyrophosphate radical when in the presence of the enzyme.

DETAILED DESCRIPTION OF THE PREFERRED EMBODIMENTS

Figure 1:
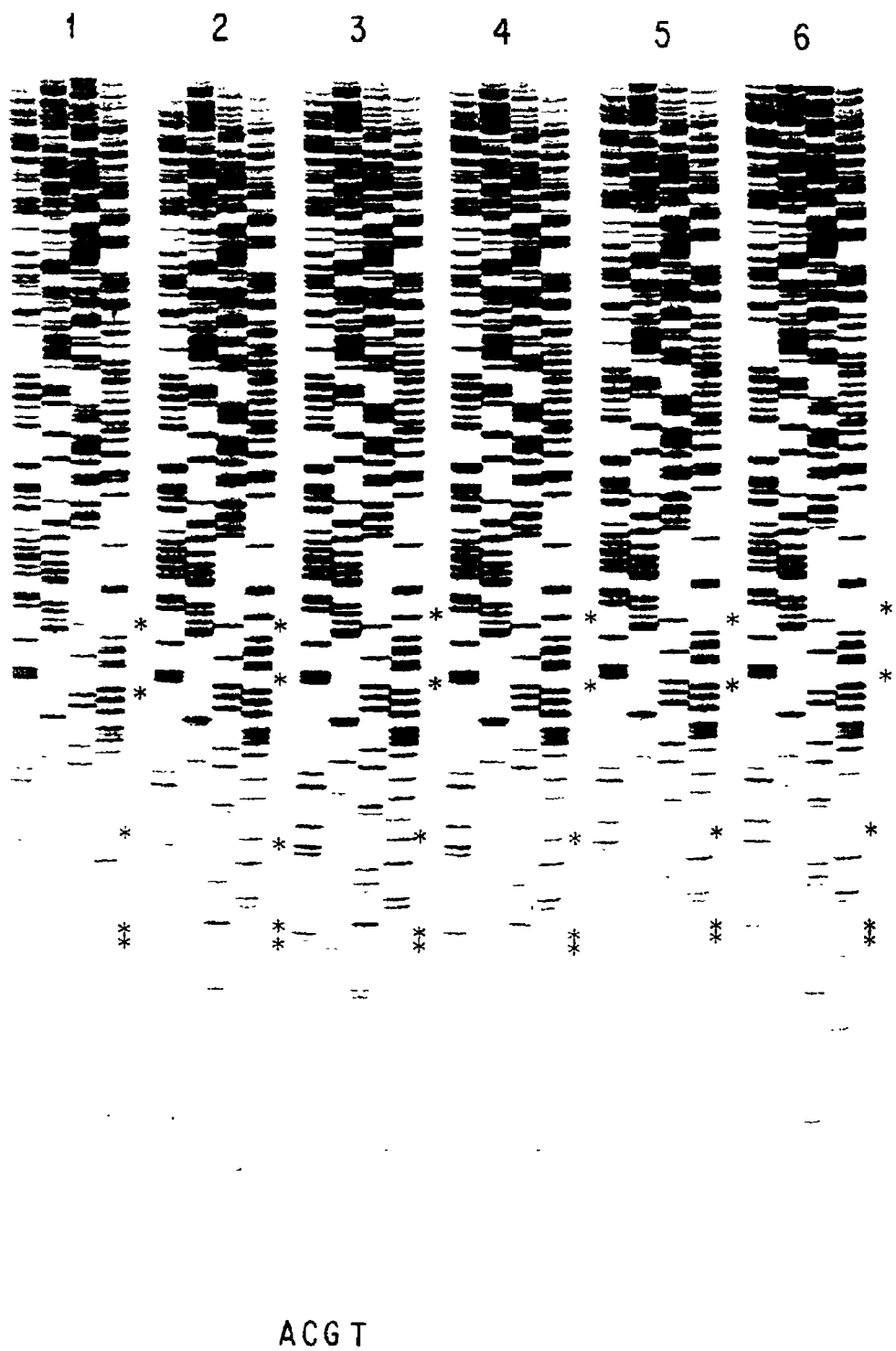
FIG. 1 depicts a gel showing the effect of UTP: glucose-1-phosphate uridylyltransferase on pyrophosphorolysis in DNA sequencing reactions.

The present invention is directed to the recognition that there are a number of enzyme reactions in a cell which utilize the high energy of a phosphodiester link in certain synthetic pathways, such as those described by Kornberg, A and Baker, T. A., in *DNA Replication,* 2nd ed., W. H. Freeman and Co., New York (1992), p. 68. These involve quite different enzymes and reactions which are distinct from the degradative inorganic pyrophosphorylase, but still prevent pyrophosphorolysis by reducing the level of pyrophosphate in the mixture. Some of the enzyme types are transferases, kinases and lyases.

The following are official enzyme classes and particular examples of enzymes that may be used in the practice of the invention:

Class EC 2.4.2.—Pentosyltransferases
    2.4.2.7 Adenine phosphoribosyltransferase
    2.4.2.10 Orotate phosphoribosyltransferase
Class EC 2.7.1.—Phosphotransferases with an alcohol group as acceptor
    2.7.1.79 Pyrophosphate: glycerol phosphotransferase
    2.7.1.80 Pyrophosphate: serine phosphotransferase
    2.7.1.90 Pyrophosphate: fructose-6-phosphate 1-phosphotransferase
    2.7.1.143 Pyrophosphate: purine nucleoside kinase
Class EC 2.7.7.—Nucleotidyltransferases
    2.7.7.4 ATP: sulfate adenylyltransferase
    2.7.7.9 UTP: glucose-1-phosphate uridylyltransferase
    2.7.7.27 ATP: glucose-1-phosphate adenylyltransferase
Class EC 4.1.1.—Carboxy-lyases
    4.1.1.38 Phosphoenolpyruvate carboxykinase
See, the *CRC Handbook of Biochemisty and Molecular Biology: Proteins* (Vol. II), Fasman, G. D., ed., 3rd edition, CRC Press, Cleveland, Ohio (1976), pp. 93–109, for the internationally developed classification system for enzymes.

For comparison, inorganic pyrophosphatase belongs to a group very distinct; hydrolases acting on phosphorous-containing acid anhydrides, with an EC classification number of 3.6.1.1.

There are many closely-related members of the 2.7.7.9 and 2.7.7.27 enzymes types that may be used in the practice of the invention. Likewise, there are many members of the 2.4.2.—enzyme type that are closely related enzymatically that may be used. Such additional enzymes are listed below:
Additional members of the 2.4.2.—subclass:
    E.C. 2.4.2.8 Hypoxanthine phosphoribosyltransferase
    E.C. 2.4.2.9 Uracil phosphoribosyltransferase
    E.C. 2.4.2.11 Nicotinate phosphoribosyltransferase
    E.C. 2.4.2.12 Nicotinamide phosphoribosyltransferase
    E.C. 2.4.2.14 Amidophosphoribosyltransferase E.C. 2.4.2.17 ATP phosphoribosyltransferase
E.C. 2.4.2.18 Anthranilate phosphoribosyltransferase
E.C. 2.4.2.19 Nicotinate-nucleotide pyrophophorylase (carboxylating)
E.C. 2.4.2.20 Dioxotetrahydropyrimidine phosphoribosyltransferase
E.C. 2.4.2.22 Xanthine-guanine phosphoribosyltransferase Additional members of 2.7.7.—subclass:
E.C. 2.7.7.1 Nicotinamide-nucleotide adenylyltransferase
E.C. 2.7.7.2 FMN adenylyltransferase
E.C. 2.7.7.10 UTP:hexose-1-phosphate uridylyltransferase
E.C. 2.7.7.11 UTP:xylose-1-phosphate uridylyltransferase
E.C. 2.7.7.13 Mannose-1-phosphate guanylyltransferase
E.C. 2.7.7.14 Ethanolamine-phosphate cytidylyltransferase
E.C. 2.7.7.15 Cholinephosphate cytidylyltransferase
E.C. 2.7.7.18 Nicotinate-nucleotide adenylyltransferase
E.C. 2.7.7.21 tRNA cytidylytransferase
E.C. 2.7.7.23 Glucosamine-1-phosphate uridylyltransferase
E.C. 2.7.7.24 Glucose-1-phosphate thymidylyltransferase
E.C. 2.7.7.25 tRNA adenylyltransferase
E.C. 2.7.7.27 Glucose-1-phosphate adenylyltranferase
E.C. 2.7.7.28 Nucleoside-triphosphate-hexose-1-phosphate nucleotidyltransferase
E.C. 2.7.7.29 Hexose-1-phosphate guanylyltransferase
E.C. 2.7.7.30 Fucose-1-phosphate guanylyltransferase
E.C. 2.7.7.32 Galactose-1-phosphate thymidylyltransferase
E.C. 2.7.7.33 Glucose-1-phosphate cytidylyltransferase
E.C. 2.7.7.34 Glucose-1-phosphate guanylyltransferase
E.C. 2.7.7.38 3-deoxy-manno-octulosonate cytidylyltransferase
E.C. 2.7.7.39 Glycerol-3-phosphate cytidylyltransferase
E.C. 2.7.7.40 D-ribitol-5-phosphate cytidylyltransferase
E.C. 2.7.7.41 Phosphatidate cytidylyltransferase
E.C. 2.7.7.42 Glutamate-ammonia-ligase adenylyltransferase
E.C. 2.7.7.43 Acylneuraminate cytidylyltransferase
E.C. 2.7.7.44 Glucuronate-1-phosphate uridylyltransferase
E.C. 2.7.7.45 Guanosine-triphosphate guanylyltransferase
E.C. 2.7.7.46 Gentamycin 2'-nucleotidyltransferase
E.C. 2.7.7.47 Streptomycin 3'-adenylyltransferase
E.C. 2.7.7.50 MRNA guanylyltransferase
E.C. 2.7.7.52 RNA uridylyltransferase
E.C. 2.7.7.54 Phenylalanine adenylyltransferase
E.C. 2.7.7.55 Anthranilate adenylyltransferase
E.C. 2.7.7.57 N-methylphosphoethanolamine cytidylyltransferase
E.C. 2.7.7.58 (2,3-dihydroxybenzoyl)adenylate synthase
E.C. 2.7.7.59 [Protein PII] uridylyltransferase A number of such enzymes have been cloned and expressed in a recombinant host. See, for example, Ladror, U. S. et al., *J. Biol. Chem.* 266:16550–16555 (1991) (Pyrophosphate: fructose-6-phosphate 1-phosphotransferase); Leyl, T. S. et al., *J. Biol. Chem.* 263:2409–2416 (1988) (ATP: sulfate adenylyltransferase); Leyh, T. S. et al., *J. Biol. Chem.* 267:10405–10410 (1992) (ATP: sulfate adenylyltransferase); Weissborn, A. C., et al., *J. Bacteriology* 176:2611–2618 (1994) (UTP:glucose-1-phosphate uridylyltransferase); Allen, T. et al., *Mol. Biochem. Parasitol* 74:99 (1995) (Adenine phosphoribosyltransferase); Vonstein, V. et al., *J. Bacteriol.* 177:4540 (1995) (Orotate phosphoribosyltransferase); Charng, Y. Y. et al., *Plant Mol. Biol.* 20:37 (1992) (Glucose-1-phosphate adenylyltransferase); Kim, D. J. and Smith, S. M., *Plant Mol. Biol.* 26:423 (1994) (Phosphoenolpyruvate carboxykinase); Jiang, Y. et al., *Exp. Parasitol.* 82:73 (1996) (Hypoxanthine-guanine phosphoribosyltransferase); Pla, J. et al., *Gene* 165:115 (1995) (ATP phosphoribosyltransferase); Feldman, R. C. et al., *Infect. Immun.* 60:166 (1992) (Uracil phosphoribosyltransferase); Vinitsky, A., *J. Bacteriol.* 173:536 (1991) (Nicotinate phosphoribosyltransferase); Ludin, K. M. et al., *Curr. Genet.* 25:465 (1994) (Amidophosphoribosyltransferase); Rose, A. B. et al., *Plant Physiol* 100:582 (1992) (Anthranilate phosphoribosyltransferase); Hughes, K. T. et al., *J. Bacteriol.* 175:479 (1993) (Quinolate phosphoribosyltransferase); Jagadeeswaran, P. et al., *Gene* 31:309 (1984) (Xanthine-guanine phosphoribosyltransferase); Nakagawa, S., *Biosci. Biotech. Biochem.* 59:694 (1995) (FMN adenylyltransferase); Marolda, C. L. and Valvano, M. A., *J. Bacteriol.* 175:148 (1993) (Mannose-1-phosphate guanylyltransferase); Kalmar, G. B., *Proc. Natl. Acad Sci. USA* 87:6029 (1990) (Choline phosphate cytidylyltransferase); Muller-Rober, B. et al., *Plant Mol. Biol.* 27:191 (1995) (Glucose-1-phosphate adenylyltransferase); Shanmugam, K. et al., *Plant Mol. Biol.* 30:281 (1996) (tRNA nucleotidyltransferase); Zapata, G. A. et al., *J. Biol. Chem.* 264:14769 (1989) (Acylneuraminate cytidylyltransferase); and Vakylenko, S. B. et al., *Antiobiot Khimioter.* 38:25 (1993) (Gentamycin 2'-nucleotidyltransferase).

Preferred enzymes which may be used in the practice of the invention are thermostable, that is, they have been isolated from thermophilic organisms or from recombinant host cells that have been transformed with DNA coding for the thermostable enzyme and derived from the thermophilic organisms. Typically, the thermostable enzymes can withstand temperatures above about 70° C. to about 100° C. for at least about a minute without losing substantially its enzymatic activity. Most preferably, the enzymes are obtained from extreme thermophiles and the thermostable enzyme is used in high temperature cycling reactions (e.g. PCR). Examples of such thermostable enzymes include phosphofructokinase from *Thermoproteus tenax* (Siebers, B. and Hensel, R., FEMS *Microbiol. Lett.* 111:1-1-8 (1993)); phosphofructokinase from *Bacillus stearothermophilus* (Zhu, X et al., *Biochem.* 34:2560–5 (1995)(the organism is not an extreme thermophile, the optimal performance with this enzyme will be in the range 60–65° C.)); uridylyltransferase from *Methanococcus jaschii* (Bult, C. J. et al., *Science* 273:1058–1072 (1996) (optimum temperature near 85° C.)); orotate phosphoribosyltransferase from *Thermus thermophilus* (Yamagishi, A et al., *Appl. Environ. Microbiol.* 62:2191–2194 (1996)); and uracil phosphoribosyltransferase from *Bacillus caldolyticus* (Ghim, S. Y. and Neuhard, J. et al., *J. Bacteriol.* 176:3698–707 (1994)).

Of course, it is necessary to also employ a substrate which is capable of either accepting a phosphate radical to give a phosphorylated product from pyrophosphate or effecting transfer of pyrophosphate radical when in the presence of the enzyme.

Examples of such enzyme/substrate combinations are shown in the following Table.

| Enzyme | Substrate |
|---|---|
| Adenine phosphoribosyltransferase | AMP |
| Orotate phosphoribosyltransferase | Orotidine 5'-phosphate |
| Pyrophosphate: glycerol phosphotransferase | Glycerol |
| Pyrophosphate: fructose-6-phosphate 1-phosphotransferase | D-Fructose-6-phosphate* |
| Pyrophosphate: purine nucleoside kinase | A purine nucleoside |
| ATP: sulfate adenylyltransferase | Adenosine 5'-phosphosulfate |
| UTP: glucose-1-phosphate uridylyltransferase | Uridine 5'-diphosphoglucose |
| Glucose-1-phosphate adenylyltransferase | ADP-glucose |
| Phosphoenolpyruvate carboxykinase | Oxaloacetate |

*Fructose-2,6-diphosphate may also be added, not as a substrate, but as a stimulator of enzyme activity.

Use of the enzyme/substrate combinations according to the present invention provide a method for preventing pyrophosphorolysis during nucleic acid synthesis, amplification or sequencing. Thus, in one embodiment, the invention relates to a method of inhibiting or preventing pyrophosphorolysis during synthesis of a nucleic acid molecule said method comprising:

(a) combining a primer with a first nucleic acid (DNA or RNA) template to give a hybridized product; and (b) incubating the hybridized product in the presence of (i) one or more nucleotides, (ii) a polymerase (DNA polymerase or RNA polymerase) and (iii) an enzyme selected from a group consisting of a pentosyltransferase, a phosphotransferase with an alcohol group as acceptor, a nucleotidyltransferase, and a carboxy-lyase under conditions sufficient to synthesize a second nucleic acid molecule (RNA or DNA) complimentary to all or a portion of said nucleic acid template.

In a second embodiment, the present invention relates to a method of sequencing a DNA molecule comprising:

(a) combining a primer with a first DNA molecule under conditions sufficient to give a hybridized product;

(b) contacting the hybridized product with one or more nucleotides, a DNA polymerase, an enzyme selected from the group consisting of a pentosyltransfurase, a phosphotransferase with an alcohol group as acceptor, a nucleotidyltransferase, and a carboxy-lyase and a terminator nucleotide, to give a reaction mixture;

(c) incubating the reaction mixture under conditions sufficient to synthesize a random population of DNA molecules complimentary to said first DNA molecule, wherein said synthesized DNA molecules are shorter in length than said first DNA molecule and wherein said synthesized DNA molecules comprise a terminator nucleotide at their 3' termini; and (d) separating said synthesized DNA molecules by size so that at least a part of the nucleotide sequence of said first DNA molecule can be determined.

In accordance with the present invention, it is possible to prevent band drop-outs in DNA sequencing. Such band drop-outs occur to varying extents in all known methods using any DNA polymerase. Thus, the invention may be used improve existing sequencing reactions for single-extension using e.g., modified T7 DNA polymerase, or for cycle sequencing, e.g., Taq-based cycle sequencing. Further, both radioactive labeling and non-radioactive labeling methods are applicable. For example, Taq-based fluorescent sequencing in the Applied Biosystems DNA Sequencer, Model 373 or 377, will suffer errors resulting from pyrophosphorolysis without reducing the pyrophosphate generated in the reaction. Prolonged incubation seems more deleterious for sequencing bands, however, implementing this invention makes the sequencing process more robust.

The dideoxy sequencing method was first described by Sanger et al., *Proc. Natl. Acad. Sci. USA* 74:5463 (1977). Improvements and modifications of the dideoxy sequencing method of Sanger et al. which may be used in the practice of the invention are described in U.S. Pat. No. 4,962,020, U.S. Pat. No. 5,498,523, U.S. Pat. Nos. 4,795,699, 5,173,411, U.S. Pat. No. 5,405,746, U.S. Pat. No. 5,003,059, U.S. Pat. No. 5,409,811, U.S. Pat. No. 5,403,709, U.S. Pat. No. 5,405,747, U.S. Pat. No. 5,411,862, U.S. Pat. No. 5,432,065, U.S. Pat. No. 5,407,799, U.S. Pat. No. 5,525,464, U.S. Pat. No. 5,525,470, U.S. Pat. No. 5,547,859, U.S. Pat. No. 5,503,980, U.S. Pat. No. 5,512,458, U.S. Pat. No. 5,308,751, U.S. Pat. No. 5,106,729, U.S. Pat. No. 5,124,247, U.S. Pat. No. 5,516,633, U.S. Pat. No. 5,484,701, U.S. Pat. No. 4,863,849, U.S. Pat. No. 5,332,666, U.S. Pat. No. 4,851,331, WO 96/14434, WO 95/20682, WO 94/16107, WO95/23236, WO94/03643, WO93/04184, WO93/20232, WO93/05060, CA 1,311,201, and EP 0409 078. See also the *M13 Cloning/Dideoxy Sequencing Instruction Manual*, BRL, Gaithersburg, Md. 20884 (1980).

In accordance with the present invention, it is also possible to prevent pyrophosphorolysis during amplification of nucleic acid molecules. Thus, the present invention relates to a method of preventing inhibition of nucleic acid synthesis during amplification of double-stranded nucleic acid molecules comprising:

(a) providing a first and second primer, wherein said first primer is complementary to a sequence at or near the 3' termini of the first strand of said nucleic acid molecule and said second primer is complementary to a sequence at or near the 3' termini of the second strand of said nucleic acid molecule;

(b) hybridizing said first primer to said first strand and said second primer to said second strand in the presence of (i) a polymerase, and (ii) an enzyme selected from the group consisting of a pentosyltransferase, a phosphotransferase with an alcohol group as an acceptor, a nucleotidyltransferase and a carboxy-lyase, under conditions such that a third nucleic acid molecule complementary to said first strand and a fourth nucleic acid molecule complementary to said second strand are synthesized;

(c) denaturing said first and third strand and said second and fourth strand; and (d) repeating steps (a) to (c) one or more times.

DNA polymerase enzymes that may be used according to the invention, e.g. dideoxy sequencing and PCR, include the wild type and mutant Tne DNA polymerases; Sequenase (T7 DNA polymerase), Taq DNA polymerase, Thermo Sequenase, *E. coli* polI and Klenow fragment, AmpliTaq FS™, T5 DNA polymerase and mutants thereof. Patents and patent applications describing these polymerases and others which may be used in the practice of the invention include U.S. Pat. No. 5,270,179 U.S. Pat. No. 5,466,591, U.S. Pat. No. 5,455,170, U.S. Pat. No. 5,374,553, U.S. Pat. No. 5,420,029, U.S. Pat. No. 5,075,216, U.S. Pat. No. 5,489,523, U.S. Pat. No. 5,474,920, U.S. Pat. No. 5,210,036, U.S. Pat. No. 5,436,326, U.S. Pat. No. 5,198,543, U.S. Pat. No. 5,108,892, U.S. Pat. No. 5,192,674, U.S. Pat. No. 5,242,818, U.S. Pat. No. 5,413,926, U.S. Pat. No. 4,767,708, U.S. Pat.

No. 5,436,149, U.S. Pat. No. 5,500,363, U.S. Pat. No. 5,352,778, U.S. Pat. No. 5,405,774, U.S. Pat. No. 5,545,552, WO 96/14417, EP O 712 927, WO95/27067, WO91/09950, WO96/14405, WO95/14770, WO95/04162, WO92/06202, WO92/06188, EP O 482 714, EP O 701 000, EP O 547 359, EP O 386 859, EP O 386 858, WO96/10640, and application Ser. No. 08/706,702, filed Sep. 6, 1996, entitled "Cloned DNA Polymerases from *Thermotoga maritima* and Mutants Thereof." Preferably, the DNA polymerase is a thermostable DNA polymerase such as Tne, Taq, or Tma and mutants thereof which exhibit little or no discrimination between dideoxynucleoside triphosphates and deoxynucleoside triphosphates, which exhibit little or no 3' to 5' exonuclease activity, and which exhibit little or no 5' to 3' exonuclease activity.

RNA polymerase enzymes that may be used according to the invention include any one of the RNA polymerase I, II or III enzymes that are described, for example, in U.S. Pat. Nos. 5,550,035, 5,102,802, 5,122,457, 5,126,251, 4,952, 496, 4,766,072, and 5,026,645; WO 95/15380, and WO 94/26911; and EP 647,716. Preferred RNA polymerase enzymes include SP6 RNA polymerase, T3 RNA polymerase and T7 RNA polymerase which are commercially available from Life Technologies, Inc. (Gaithersburg, Md.).

Chain terminators for DNA synthesis and sequencing reactions are listed in the following Table.

| Type of nucleoside triphosphate | DNA polymerase tested | Reference |
|---|---|---|
| ribonucleoside 5'-triphosphate | Calf thymus TdT | Beabealashvilli et al., Biochim. Biophys. Acta 868:136–144 (1986). |
| ribonucleoside 5'-triphosphate | *E. coli* DNA Polymerase I | Chidgeavadze et al., Biochim. Biophys. Acta 868:145–152 (1986). |
| arabinonucleoside 5'-triphosphate | Calf thymus TdT Reverse transcriptase | Beabealashvilli et al. Biochim. Biophys. Acta 868:136–144 (1986). |
| 3'-amino-3'-deoxyarabinonucleoside 5'-triphosphate | T4 DNA Polymerase | Chidgeavadze et al., Biochim. Biophys. Acta 868:145–152 (1986). |
| 2'-deoxy-2'-aminoribonuoleoside 5'-triphosphate | *E. coli* DNA Polymerase I | Chidgeavadze et al, Biochim. Biophys. Acta 868:145–152 (1986). |
| 3'-azido-2',3'-dideoxyribonucleoside 5'-triphosphate | Reverse transcriptase | Beabealashvilli et al., Biochim. Biophys. Acta 868:136–144 (1986). |
| 3'-azido-2',3'-dideoxyribonucleoside 5'-triphosphate | *E. coli* DNA polymerase I | Pyrinova et al., Molekulyarnaya Biologiya 22:1405–1410 (1988). |
| 3'-amino-2',3'-dideoxyribonucleoside 5'-triphosphate | *E. coli* DNA Polymerase I Calf thymus DNA Pol. α Rat liver polymerase β | Chidgeavadze et al., Nucl. Acids Res. 12:1671–1686 (1984). |
| 3'-amino-2',3'-dideoxyribonucleoside 5'-triphosphate | Calf thymus TdT Reverse transcriptase | Beabealashvilli et al., Biochim. Biophys. Acta 868:136–144 (1986). |
| 3'-amino-2',3'-dideoxyribonucleoside 5'-triphosphate | *E. coli* DNA Polymerase I Calf thymus DNA Pol. α | Chidgeavadze et al, Biochim. Biophys. Acta 868:145–152 (1986). |
| 3'-N-acetylamino-2',3'-dideoxyribonucleoside 5'-triphosphate | Calf thymus TdT Reverse transcriptase | Beabealashvilli et al., Biochim. Biophys. Acta 868:136–144 (1986). |
| 3'-N-acetylamino-2',3'-dideoxyribonucleoside 5'-triphosphate | *E. coli* DNA Polymerase I | Chidgeavadze et al, Biochim. Biophys. Acta 868:145–152 (1986). |
| 3'-fluorescaminyl-2',3'-dideoxyribonucleoside 5'-triphosphate | Reverse transcriptase | Beabealashvilli et al., Biochim. Biophys. Acta 868:136–144 (1986). |
| 3'-fluorescaminyl-2',3'-dideoxyribonucleoside 5'-triphosphate | *E. coli* DNA Polymerase I Calf thymus DNA Pol. α | Chidgeavadze et al, Biochim. Biophys. Acta 868:145–152 (1986). |
| 3'-N-biotinylamino-2',3'-dideoxyribo-nucleoside 5'-triphosphate | Calf thymus TdT Reverse transcriptase | Beabealashvilli et al., Biochim. Biophys. Acta 868:136–144 (1986). |
| 3'-N-biotinylamino-2',3'-dideoxyribo-nucleoside 5'-triphosphate | *E. coli* DNA Polymerase I Calf thymus DNA Pol. α | Chidgeavadze et al, Biochim. Biophys. Acta 868:145–152 (1986). |
| 3'-amino-3'-deoxyarabinonucleoside 5'-triphosphate | Calf thymus TdT Reverse transcriptase | Beabealashvilli et al., Biochim. Biophys. Acta 868:136–144 (1986). |
| 3'-azido-3'-deoxyarabinonucleoside 5'-triphosphate | Reverse transcriptase | Beabealashvilli et al., Biochim. Biophys. Acta 868:136–144 (1986). |
| 2'-deoxy-3'-O-methylribonucleoside 5'-triphosphate | Reverse transcriptase | Beabealashvilli et al., Biochim. Biophys. Acta 868:136–144 (1986). |
| 2'-deoxy-3'-O-methylribonucleoside 5'- | AMV reverse transcriptase | Kutateladze et al., FEBS Lett. 207:205–212 (1986). |

-continued

| Type of nucleoside triphosphate | DNA polymerase tested | Reference |
| --- | --- | --- |
| 2',3'-dideoxy-3'-fluororibonucleoside 5'-triphosphate | E. coli DNA Polymerase I<br>AMV reverse transcriptase<br>Calf thymus TdT | Chidgeavadze et al., FEBS Lett. 183:275–278 (1985). |
| 2',3'-dideoxy-3'-fluororibonucleoside 5'-triphosphate | Reverse transcriptase | Beabealashvilli et al., Biochim. Biophys. Acta 868:136–144 (1986). |
| 2',3'-dideoxy-3'-fluororibonucleoside 5'-triphosphate | T4 DNA Polymerase | Chidgeavadze et al, Biochim. Biophys. Acta 868:145–152 (1986). |
| 2',3'-didehydro-2',3'-dideoxyribonucleoside 5'-triphosphate | E. coli polymerase I KF<br>Rat liver DNA polymerase β<br>AMV reverse transcriptase<br>RSV reverse transcriptase<br>Calf thymus TdT | Dyatkina et al., FEBS Lett. 219:151–155 (1987). |
| 3'-chloro-2',3'-dideoxyribonucleoside 5'-triphosphate | E. coli DNA polymerase I,<br>Rat liver DNA Polymerase β<br>AMV reverse transcriptase<br>RSV reverse transcriptase<br>Calf thymus TdT | Krayevsky et al., Nucleosides and Nucleotides 7:613–617 (1988). |
| 3'-methylsulfonamido-2',3'-dideoxy-ribonucleoside 5'-triphosphate | AMV reverse transcriptase | Krayevsky et al., Nucleosides and Nucleotides 7:613–617 (1988). |
| 2',3'-di-O-isopropylideneribo-nucleoside 5'-triphophate | AMV reverse transcriptase | Krayevsky et al., Nucleosides and Nucleotides 7:613–617 (1988). |

The term "nucleotide" includes deoxyribonucleoside triphosphates such as dATP, dCTP, dITP, dUTP, dGTP, dTTP, or derivatives thereof Such derivatives include, for example [αS]dATP, 7-deaza-dGTP and 7-deaza-dATP. The term "nucleotide" as used herein also refers to ribonucleoside triphosphates (rNTPs) and their derivatives. Illustrated examples of ribonucleoside triphosphates include, but are not limited to, ATP, CTP, GTP, ITP and UTP.

This invention may also be used in methods where improvement of synthesis of nucleic acids by a polymerase is desired and where pyrophosphorolysis is deemed counter-productive. Uses include: polymerase chain reaction, especially 'Long PCR,' and cDNA synthesis. Examples of patents describing these methods include U.S. Pat. No. 4,965,188, U.S. Pat. No. 5,079,352, U.S. Pat. No. 5,091,310, U.S. Pat. No. 5,142,033, U.S. Pat. No. 4,683,195, U.S. Pat. No. 4,683,202, U.S. Pat. No. 4,800,159, U.S. Pat. No. 5,512,462 and U.S. Pat. No. 5,405,776. In the case of cDNA synthesis, a reverse transcriptase polymerase is incubated with the mRNA template, the deoxynucleoside triphosphates and the enzyme which prevents the build up of pyrophosphate.

The invention also relates to a kit comprising a container means such as a box having in close confinement therein two or more container means such as vials, ampules, tubes, jars and the like, each of which contain the materials necessary to carry out the invention. For example, a first container means may comprise an enzyme selected from the group consisting of a pentosyltransferase, a phosphotransferase with an alcohol group as acceptor, a nucleotidyltransferase, and a carboxy-lyase. This first container means may also comprise a DNA or RNA polymerase. Alternatively, a second container means may comprise the DNA or RNA polymerase. A third container means will comprise a substrate which is capable of either accepting a phosphate radical to give a phosphorylated product from pyrophosphate or effecting transfer of pyrophosphate when in the presence of the enzyme. Other container means may contain other reagents that are necessary for carrying out dideoxy sequencing or PCR as are well known.

Preferably, the contents of the container means are present at working concentrations (e.g. 1×). Other container means may contain other reagents that are necessary for carrying out dideoxy sequencing or amplification (PCR). Methods for preparing such compositions at working concentrations are described in application Ser. No. 08/689,815, filed Aug. 14, 1996, entitled "Stable Compositions for Nucleic Acid Sequencing and Amplification."

The enzyme and substrate used for reducing pyrophosphate concentration may be mixed directly with the polymerase at their appropriate concentrations, which in turn may be further mixed with reaction buffer and nucleotides. In general, the enzymes and substrate are present at concentrations sufficient to reduce the level of pyrophosphate in nucleic acid synthesis, amplification or sequencing reactions. Preferably, the enzymes and substrate are present at concentrations which reduce the level of pyrophosphate and, as a result, prevent pyrophosphorolysis (e.g., reduce the inhibition of amplification reactions and/or reduce or eliminate band drop out in sequencing reactions). Particular concentrations of the enzyme will vary according to the activity of the enzyme and the temperature of the reaction. Additionally, in high temperature cycling reactions (PCR), it may be necessary to add enzyme after each cycle if the enzyme is inactivated by the cycle temperature. By way of illustration, when the enzyme is UTP: glucose-1-phosphate uridylyltransferase, the polymerase is Sequenase Version 2.0, and the temperature of the reaction is 37° C., the concentration of UTP: glucose-1-phosphate uridylyltransferase may range from about 0.01 U/$\mu$l to about 15 U/$\mu$l, preferably about 0.15 U/$\mu$l. The concentration of the uridine 5'-diphosphoglucose may range from about 10 $\mu$M to about 0.5 M, preferably about 190 $\mu$M. If instead the enzyme is ATP: sulfate adenylyltransferase, the concentration of ATP: sulfate adenylyltransferase may range from about 0.001 U/$\mu$l to about 2 U/$\mu$l, preferably about 0.002 U/$\mu$l, and the concentration of adenosine 5'-phosphosulfate may range from about 0.25 $\mu$M to about 0.5 M, preferably about 5 $\mu$M.

If the enzyme is Pyrophosphate: fructose-6-phosphate 1-phosphotransferase, the concentration of Pyrophosphate: fructose-6-phosphate 1-phosphotransferase may range from about 0.00004 U/µl to about 4 U/µl, and the concentration of fructose-6-phosphate may range from about 10 µM to about 0.5 M, preferably about 190 µM. The concentration of the stimulatory cofactor fructose-2,6-diphosphate may range from about 0.5 nM to about 100 µM, preferably about 50 nM.

Thus, the solution of the present invention is an aqueous and/or buffered liquid containing the components described above. These components are present in the solution at concentrations sufficient to perform their desired function. If the reaction mixture is intended to amplify a target nucleic acid molecule, the reaction mixture will contain the enzyme which reduces the level of pyrophosphate, the substrate which is capable of either accepting a phosphate radical to give a phosphorylated substrate from pyrophosphate or effecting transfer of pyrophosphate when in the presence of the enzyme, a DNA polymerase, all four dNTPs, the one or two oligonucleotide primers having a single stranded region (and optionally a double stranded region) which are capable of annealing to the target nucleic acid molecule, being extended and thereby amplified. The primer extension reaction may also comprise a chain terminator as described herein, e.g. a dideoxynucleoside triphosphate, which allows for sequencing of the target DNA molecule by the well known Sanger dideoxy sequencing method.

In general, the enzymes described in this invention are ubiquitous in nature so different versions of any one enzyme could be obtained from different organisms for different reaction situations. For example, a sub-room temperature reaction may be preferred, where an enzyme from a cryophile may be appropriate. Alternatively, thermostable enzymes may be utilized. Further, many examples of enzymes using pyrophosphate as a co-substrate are known, so many different versions of this invention are anticipated. For example, the best conditions to enhance Long PCR may not be the same as for DNA sequencing, thus a different enzyme may be needed for each application. The variety of enzymes and sources permits flexibility in optimal design of application of the invention.

The invention is based on enzymatic removal of the pyrophosphate concomitant with nucleic acid synthesis. Some enzymes may not be compatible with the reaction environment preferred for nucleic acid synthesis, e.g., pH, monovalent cation concentration, or Tris buffer. Many different enzymes exist which are anticipated to provide the needed reduction of pyrophosphate concentration. Thus, an appropriate enzyme can be found that would be compatible without requiring compromise of optimal nucleic acid synthesis conditions. Two examples are already provided in the literature (Nyren, ibid and Johnson et al, ibid).

In the Examples which follow, either UTP: glucose-1-phosphate uridylyltransferase and uridine-5'-diphosphoglucose, or ATP: sulfate adenylyltransferase and adenosine 5'-phosphosulfate, or Pyrophosphate: fructose-6-phosphate 1-phosphotransferase and fructose-6-phosphate, were used in a Sequenase™ reaction incubated for 30 minutes without observing drop-out bands. Without both enzyme and substrate, many drop-out bands are evident in a 30-minute incubation.

Having now generally described the invention, the same will be more readily understood through reference to the following Examples which are provided by way of illustration, and are not intended to be limiting of the present invention, unless specified.

EXAMPLES

Example 1

Use of UTP: glucose-1-phosphate uridylytransferase to eliminate pyrophosphorolysis in DNA sequencing Template and primer sufficient for 7 sequencing reactions were annealed in a 39 µl reaction volume by incubating for two minutes at 65° C. in a heating block and then slowly cooling the reaction to less than 37° C. The composition of the reaction was: 74 nM M13 mp19(+) strand DNA, 90 nM M13/pUC 23 base Forward Sequencing Primer, 72 mM Tris-HCl (pH 7.5), 45 mM NaCl, 18 nM MgCl$_2$. Six separate reactions were then radiolabeled by incubating the following 15.5 µl reactions at room temperature (23–24° C.) for 2 minutes: 26.5 nM M13 Mp19(+) strand DNA, 32 nM M13/pUC 23 base Forward Sequencing Primer, 129 mM Tris-HCl (pH 7.5), 32 mM NaCl, 13 mM MgCl$_2$, 6.5 mM DTT, 0.32 µM (0.32 µCi/µl) [α-$^{35}$S]dATP, 0.194 µM dCTP, 0.194 µM 7-deaza-dGTP, 0.194 µM dTTP, 0.21 U/µl Sequenase Version 2.0 T7 DNA Polymerase. Additional components were present in the indicated reactions at the concentrations given in the following table:

| Reaction Number | Concentration of Inorganic Pyrophosphatase (U/µl) | Concentration of uridine-5'-diphosphoglucose* (µM) | Concentration of UTP: glucose-1-phosphate uridylyltransferase (U/µl)** |
|---|---|---|---|
| 1 | 0 | 0 | 0 |
| 2 | 0.00004 | 0 | 0 |
| 3 | 0 | 320 | 0.016 |
| 4 | 0 | 320 | 0.0032 |
| 5 | 0 | 320 | 0.00065 |
| 6 | 0 | 0 | 0.0032 |

*uridine-5'-diphosphoglucose (Cat. No. U-4625) Sigma
**UTP: glucose-1-phosphate uridylyltransferase (Cat. No. U-5877) Sigma Each mixture was then divided into four tubes for completion of base-specific termination reactions. These sets of reactions were incubated for 30 minutes at 37° C. and had the following compositions in 6 µl reaction volumes: 15.4 nM M13 mp19(+) strand DNA, 18.5 nM M13/pUC 23 base Forward Sequencing Primer, 75 mM Tris-HCl (pH 7.5), 40 mM NaCl, 7.5 mM MgCl$_2$, 3.8 mM DTT, 0.19 µM (0.19 µCi/µl) [α-$^{35}$S]dATP, 33.3 µM dATP, 33.4 µM dCTP, 33.4 µM 7-deaza-dGTP, 33.4 µM dTTP, 0.12 U/µl Sequenase Version 2.0, T7 DNA Polymerase, and 3.3 µM ddATP, ddCTP, ddGTP or ddTTP. Additional components were present in the indicated reaction sets at the concentrations given in the following table:

| Reaction Number | Concentration of Inorganic Pyrophosphatase (U/µl) | Concentration of uridine-5'-diphosphoglucose (µM) | Concentration of UTP: glucose-1-phosphate uridylyltransferase (U/µl) |
|---|---|---|---|
| 1 | 0 | 0 | 0 |
| 2 | 0.00002 | 0 | 0 |
| 3 | 0 | 187 | 0.0093 |
| 4 | 0 | 187 | 0.0019 |
| 5 | 0 | 187 | 0.00038 |
| 6 | 0 | 0 | 0.0019 |

Reactions were stopped by adding 4 µL of 95% formamide, 20 µM EDTA, 0.05% bromophenol blue and 0.05% xylene cyanol FF and denatured for 2 minutes at 70°

C. Three-microliter aliquots were separated on a 6% TBE-7 M urea sequencing gel. The dried gel was exposed to Kodak BioMAX x-ray film at room temperature for approximately 18 hours.

Results from these six sets of reactions are shown in the photograph of the gel (FIG. 1), where each set are separately displayed, left to right, in the order 1 through 6 as described in the above table. Under conditions where neither UTP: glucose-1-phosphate uridylyltransferase nor inorganic pyrophosphatase were present in the reactions (set 1), certain sequencing bands are either faintly or not visible as indicated by an asterisk on the figure. When UTP: glucose-1-phosphate uridylyltransferase is added at two different enzyme concentrations (sets 3–4), the bands are fully visible. In the presence of a lower concentration of this enzyme (set 5), only partial recovery of the bands is seen. Even though UTP: glucose-1-phosphate uridylyltransferase was present in set 6, the absence of the enzyme substrate uridine 5'-diphosphoglucose prevented the enzyme from reacting with pyrophosphate and providing protection from band loss. The inhibition of pyrophosphorolysis demonstrated in this example is dependent on both enzyme and enzyme substrate and is not the result of a contaminating pyrophosphatase-type activity. For reference, the action of inorganic pyrophosphatase in protecting from band loss is shown in set 2.

Example 2

Use of ATP: sulfate adenylyltransferase to eliminate pyrophosphorolysis in DNA sequencing Template and primer sufficient for 7 sequencing reactions were annealed in a 70 μl reaction volume by incubating for two minutes at 65° C. in a heating block and then slowly cooling the reaction to less than 37° C. The composition of the reaction was: 41 nM M13 mp19(+) strand DNA, 50 nM M13/pUC 23 base Forward Sequencing Primer, 200 mM Tris-HCl (pH 7.5), 50 mM NaCl, 20 mM MgCl$_2$. Five separate reactions were then radiolabeled by incubating the following 15.5 μl reactions at room temperature (23–24° C.) for 2 minutes: 26.5 nM M13 mp19(+) strand DNA, 32 mM M13/pUC 23 base Forward Sequencing Primer, 129 mM Tris-HCl (pH 7.5), 32 mM NaCl, 13 mM MgCl$_2$, 6.5 mM DTT, 0.32 μM (0.32 μCi/μl) [α-$^{35}$S]dATP, 0.194 μM dCTP, 0.194 μM 7-deaza-dGTP, 0.194 μM dTTP, 0.21 U/μl Sequenase Version 2.0 T7 DNA Polymerase. Additional components were present in the indicated reaction sets at the concentrations given in the following table:

| Reaction Number | Concentration of Inorganic Pyrophosphatase (U/μl) | Concentration of adenosine 5'-phosphosulfate* (μM) | Concentration of ATP: sulfate adenylyltransferase **(U/μl) |
|---|---|---|---|
| 1 | 0 | 0 | 0 |
| 2 | 0.00004 | 0 | 0 |
| 3 | 0 | 8.4 | 0.0016 |
| 4 | 0 | 8.4 | 0.0032 |
| 5 | 0 | 0 | 0.0032 |

*adenosine 5'-phosphosulifate (Cat. No. A-5508) Sigma
**ATP: sulfate adenylyltransferase (Cat. No. A-8957) Sigma Each mixture was then divided into four tubes for completion of base-specific termination reactions. These sets of reactions were incubated for 30 minutes at 37° C. and had the following compositions in 6 μl reaction volumes: 15.4 nM M13 mp19(+) strand DNA, 18.5 nM M13/pUC 23 base Forward Sequencing Primer, 75 mM Tris-HCl (pH7.5), 40 mM NaCl, 7.5 mM MgCl, 3.8 mM DTT, 0.19 μM (0.19 μCi/μl) [α-$^{35}$S]dATP, 33.3 μM dATP, 33.4 μM dCTP, 33.4 μM 7-deaza-dGTP, 33.4 μM dTTP, 0.12 U/μl Sequenase Version 2.0 T7 DNA Polymerase, and 3.3 μM ddATP, ddCTP, ddGTP or ddTTP. Additional components were present in the indicated reactions at the concentrations given in the following table:

| Reaction Number | Concentration of Inorganic Pyrophosphatase (U/μl) | Concentration of adenosine 5'-phosphosulfate (μM) | Concentration of ATP: sulfate adenylyltransferase (U/μl) |
|---|---|---|---|
| 1 | 0 | 0 | 0 |
| 2 | 0.00002 | 0 | 0 |
| 3 | 0 | 4.9 | 0.0093 |
| 4 | 0 | 4.9 | 0.0019 |
| 5 | 0 | 0 | 0.0019 |

Reactions were stopped by adding 4 μl of 95% formamide, 20 mM EDTA, 0.05% bromophenol blue and 0.05% xylene cyanol FF and denatured for 2 minutes at 70° C. Three-microliter aliquots were separated on a 6% TIBE-7M urea sequencing gel. The dried gel was exposed to Kodak BioMAX x-ray film at room temperature for approximately 18 hours.

Figure 2:
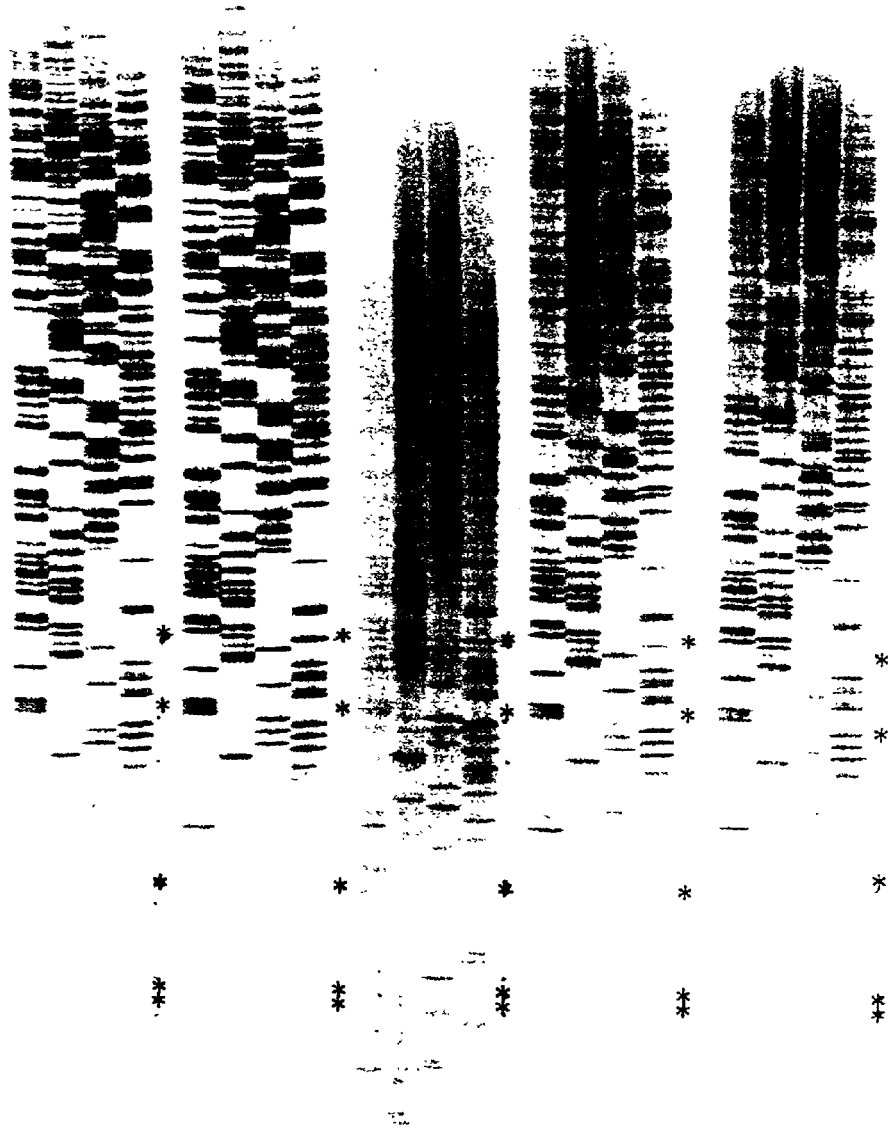
FIG. 2 depicts a gel showing the effect of ATP: sulfate adenylyltransferase on pyrophosphorolysis in DNA sequencing reactions.

Results from these five sets of reactions are shown in the photograph of the gel (FIG. 2), where each set are separately displayed, left to right, in the order 1 through 5 as described in the above table. Under conditions where neither ATP: sulfate adenylyltransferase nor inorganic pyrophosphatase were present in the reactions (set 1), certain sequencing bands are either faintly or not visible as indicated by an asterisk on the figure. When ATP: sulfate adenylyltransferase is added (set 3), the bands are fully visible. In the presence of a lower concentration of this enzyme (set 4), only partial recovery of the bands is seen. Even though ATP: sulfate adenylyltransferase was present in set 5, the absence of the enzyme substrate adenosine 5'-phosphosulfate prevented the enzyme from reacting with pyrophosphate and providing protection from band loss. Since the preparation of ATP: sulfate adenylyltransferase used in this example was contaminated with deoxyribonucleases, the presence of some non-specific DNA fragment sizes (smearing) in the gel causes an increase in the background, but does not prevent the demonstration of the effectiveness of ATP: sulfate adenylyltransferase from removing pyrophosphate from the sequencing reactions. The inhibition of pyrophosphorolysis demonstrated in this example is dependent on both enzyme and enzyme substrate and is not the result of a contaminating pyrophosphatase-type activity. For reference, the action of inorganic pyrophosphatase in protecting from band loss is shown in set 2.

Example 3

Use of Pyrophosphate: fructose-6-phosphate 1-phosphotransferase to eliminate pyrophosphorolysis in DNA sequencing Template and primer sufficient for 7 sequencing reactions were annealed in a 39 μl reaction volume by incubating for two minutes at 65° C. in a heating block and then slowly cooling the reaction to less than 37° C. The composition of the reaction was: 74 nM M13 mp19(+) strand DNA, 90 nM M13/pUC 23 base Forward Sequencing Primer, 360 mM Tris-HCl (pH 7.5), 90 mM NaCl, 36 mM MgCl$_2$. Seven separate reactions were then radiolabeled by incubating the following 15.5 μl reactions at room temperature (23–24° C.) for 2 minutes: 26.5 nM M13 mp19(+) strand DNA, 32 nM M13/pUC 23 base Forward Sequencing Primer, 129 mM Tris-HCl (pH 7.5), 32 mM NaCl, 13 mMMgCl$_2$, 6.5 mM DTT, 0.32 µM (0.32 µCi/µl) [α-$^{35}$S]dATP, 0.194 µM dCTP, 0.194 µM 7-deaza-dGTP, 0.194 µM dTTP, 0.21 U/µl Sequenase Version 2.0 T7 DNA Polymerase. Additional components were present in the indicated reactions at the concentrations given in the following table:

| Reaction Number | Concentration of Inorganic Pyrophosphatase (U/µl) | Concentration of Fructose-6-phosphate* (mM) | Concentration of Fructose-2,6-diphosphate (µM) | Concentration of Pyrophosphate: fructose-6-phosphate 1-phosphotransferase* (U/µl) |
|---|---|---|---|---|
| 1 | 0 | 0 | 0 | 0 |
| 2 | 0.00004 | 0 | 0 | 0 |
| 3 | 0 | 0.32 | 0.09 | 0.0032 |
| 4 | 0 | 0.32 | 0.09 | 0.00065 |
| 5 | 0 | 0.32 | 0.09 | 0.00032 |
| 6 | 0 | 0 | 0.09 | 0.0032 |
| 7 | 0 | 0 | 0.09 | 0.00065 |

*Fructose-6-phosphate (Cat. No. F-3627) Sigma
**Fructose-2,6-diphosphate (Cat. No. F-7006) Sigma
***Pyrophosphate: fructose-6-phosphate 1-phosphotransferase, from Mung Bean (Cat. No. F-8757)

Each mixture was then divided into four tubes for completion of base-specific termination reactions. These sets of reactions were incubated for 30 minutes at 37° C. and had the following compositions in 6 µl reaction volumes: 15.4 nM M13 mp19(+) strand DNA, 18.5 nM M13/pUC 23 base Forward Sequencing Primer, 75 mM Tris-HCl (pH 7.5), 40 mM NaCl, 7.5 mm MgCl$_2$, 3.8 mM DTT, 0.19 µM (0.19 µCi/µl) [α-$^{35}$S]dATP, 33.3 µM dATP, 33.4 µM dCTP, 33.4 µM 7-deaza-dGTP, 33.4 µM dTTP, 0.12 U/µl Sequenase Version 2.0 T7 DNA Polymerase, and 3.3 µM ddATP, ddCTP, ddGTP or ddTTP. Additional components were present in the indicated reactions at the concentrations given in the following table:

| Reaction Number | Concentration of Inorganic Pyrophosphatase (U/µl) | Concentration of Fructose-6-phosphate (mM) | Concentration of Fructose-2,6-diphosphate (µM) | Concentration of Pyrophosphate: fructose-6-phosphate 1-phosphotransferase (U/µl) |
|---|---|---|---|---|
| 1 | 0 | 0 | 0 | 0 |
| 2 | 0.00002 | 0 | 0 | 0 |
| 3 | 0 | 0.19 | 0.05 | 0.0019 |
| 4 | 0 | 0.19 | 0.05 | 0.00038 |
| 5 | 0 | 0.19 | 0.05 | 0.00019 |
| 6 | 0 | 0 | 0.05 | 0.0019 |
| 7 | 0 | 0 | 0.05 | 0.00038 |

Reactions were stopped by adding 4 µl of 95% formamide, 20 mM EDTA, 0.05% bromophenol blue and 0.05% xylene cyanol FF and denatured for 2 minutes at 70° C. Three-microliter aliquots were separated on a 6% TBE-7 M urea sequencing gel. The dried gel was exposed to Kodak BioMAX x-ray film at room temperature for approximately 18 hours.

Figure 3:
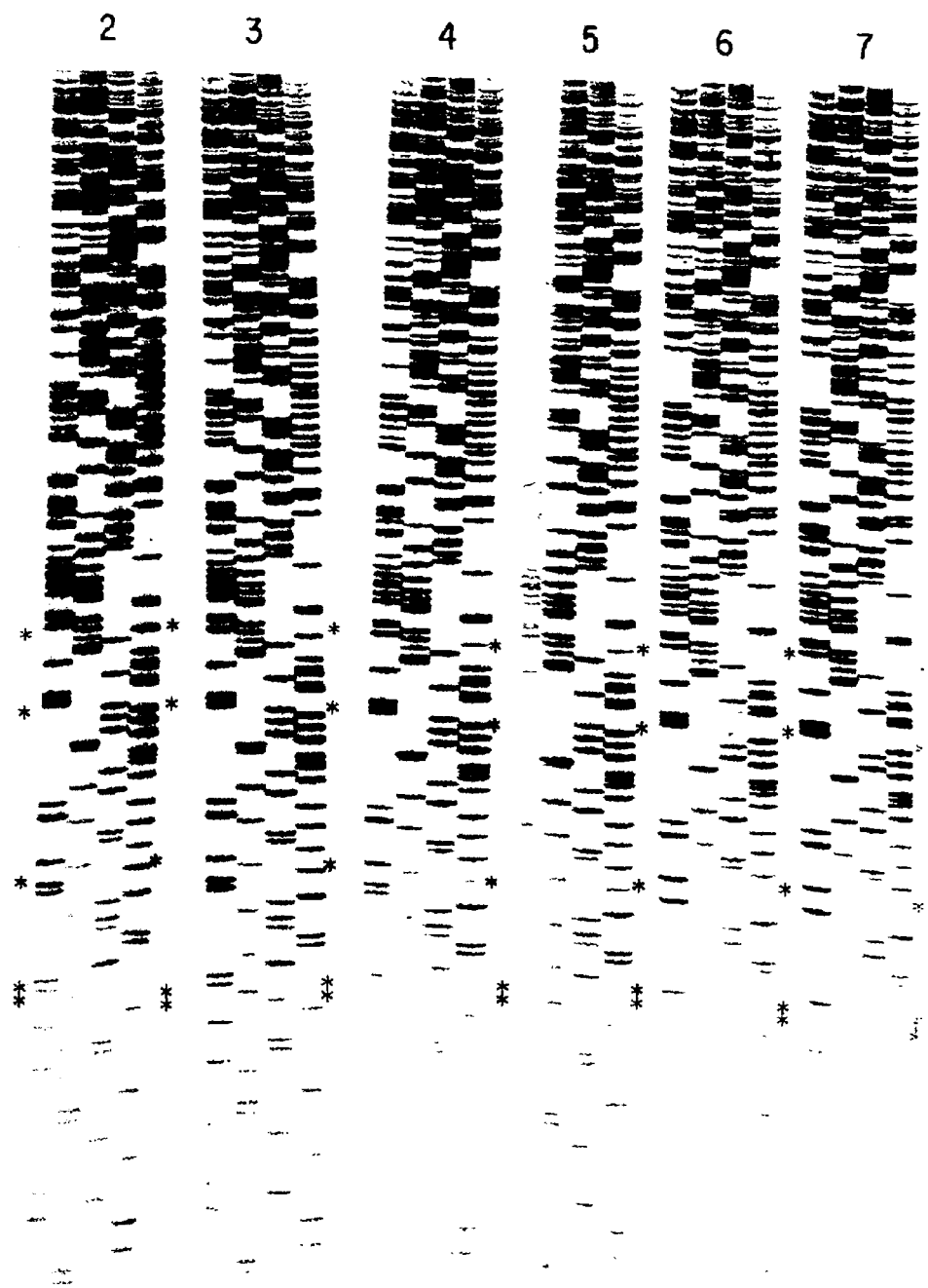
FIG. 3 depicts a gel showing the effect of Pyrophosphate: fructose-6-phosphate 1-phosphotransferase on pyrophosphorolysis in DNA sequencing reactions.

Results from these seven sets of reactions are shown in the photograph of the gel (FIG. 3), where each set are separately displayed, left to right, in the order 1 through 7 as described in the above table. Under conditions where neither Pyrophosphate: fructose-6-phosphate 1-phosphotransferase nor inorganic pyrophosphatase were present in the reactions (set 1), certain sequencing bands are either faintly or not visible as indicated by an asterisk on the figure. When Pyrophosphate: fructose-6-phosphate 1-phosphotransferase is added (set 3), the bands are fully visible. In the presence of lower concentrations of this enzyme (sets 4–5), only partial recovery of the bands is seen. Even though Pyrophosphate: fructose-6-phosphate 1-phosphotransferase was present at two different concentrations in sets 6 and 7, the absence of the enzyme substrate fructose-6-phosphate prevented the enzyme from reacting with pyrophosphate and providing protection from band loss. The inhibition of pyrophosphorolysis demonstrated in the example is dependent on both enzyme and enzyme substrate and is not the result of a contaminating pyrophosphatase-type activity. For reference, the action of inorganic pyrophosphatase in protecting from band loss is shown in set 2.

From the foregoing description, one skilled in the art can easily ascertain the essential characteristics of this invention, and without departing from the spirit and scope thereof, can make various changes and modifications of the invention to adapt it to various usages and conditions without undue experimentation. All patents, patent applications and publications cited herein are incorporated by reference in their entirety.

What is claimed is:

1. A method of making at least one nucleic acid molecule, said method comprising
   (a) combining, in a mixture, at least one nucleic acid template, at least one polymerase or at least one reverse transcriptase, and an enzyme selected from the group consisting of a pentosyltransferase, a phosphotransferase with an alcohol group as acceptor, a nucleotidyltransferase, and a carboxy-lyase; and
   (b) incubating said mixture under conditions sufficient to make one or more first nucleic acid molecules complementary to all or a portion of said nucleic acid template.

2. The method of claim 1, wherein said enzyme is a pentosyltransferase.

3. The method of claim 2, wherein said enzyme is an adenine phosphoribosyltransferase or an orotate phosphoribosyltransferase.

4. The method of claim 1, wherein said enzyme is a phosphotransferase with an alcohol group as acceptor.

5. The method of claim 4, wherein said enzyme is a pyrophosphate: glycerol phosphotransferase, a pyrophosphate: serine phosphotransferase, a pyrophosphate: fructose-6-phosphate 1-phosphotransferase or a pyrophosphate: purine nucleoside kinase.

6. The method of claim 1, wherein said enzyme is a nucleotidyltransferase.

7. The method of claim 6, wherein said enzyme is an ATP: sulfate adenylyltransferase, a UTP: glucose-1-phosphate uridylyltransferase or an ATP: glucose-1-phosphate adenylyltransferase.

8. The method of claim 1, wherein said enzyme is a carboxy-lyase.

9. The method of claim 8, wherein said enzyme is a phosphoenolpyruvate carboxykinase.

10. The method of claim 1, wherein said reverse transcriptase is a retroviral reverse transcriptase.

11. The method of claim 1, wherein said reverse transcriptase is an AMV reverse transcriptase or a RSV reverse transcriptase.

12. The method of claim 1, further comprising:
   (c) incubating said one or more first nucleic acid molecules under conditions sufficient to synthesize one or more second nucleic acid molecules complementary to all or a portion of said one or more first nucleic acid molecules.

13. The method of claim 12, further comprising amplifying said first nucleic acid molecules or said second nucleic acid molecules.

14. The method of claim 1, wherein said polymerase is an RNA polymerase or a DNA polymerase.

15. The method of claim 14, wherein said DNA polymerase is thermostable.

16. A composition comprising:
   (a) an enzyme selected from the group consisting of a pentosyltransferase, a phosphotransferase with an alcohol group as acceptor, a nucleotidyltransferase, and a carboxy-lyase; and
   (b) at least one polymerase or at least one reverse transcriptase.

17. The composition of claim 16, wherein said enzyme of (a) is a pentosyltransferase.

18. The composition of claim 17, wherein said enzyme of (a) is an adenine phosphoribosyltransferase or an orotate phosphoribosyltransferase.

19. The composition of claim 16, wherein said enzyme of (a) is a phosphotransferase with an alcohol group as acceptor.

20. The composition of claim 19, wherein said enzyme of (a) is a pyrophosphate: glycerol phosphotransferase, a pyrophosphate: serine phosphotransferase, a pyrophosphate: fructose-6-phosphate 1-phosphotransferase or a pyrophosphate: purine nucleoside kinase.

21. The composition of claim 16, wherein said enzyme of (a) is a nucleotidyltransferase.

22. The composition of claim 21, wherein said enzyme is an ATP: sulfate adenylyltransferase, a UTP: glucose-1-phosphate uridylyltransferase or an ATP: glucose-1-phosphate adenylyltransferase.

23. The composition of claim 16, wherein said enzyme of (a) is a carboxy-lyase.

24. The composition of claim 23, wherein said enzyme of (a) is a phosphoenolpyruvate carboxykinase.

25. The composition of claim 16, further comprising a substrate which is capable of either accepting a phosphate radical to give a phosphorylated product from pyrophosphate or effecting transfer of pyrophosphate when in the presence of said enzyme of (a).

26. The composition of claim 16, wherein said reverse transcriptase is a retroviral reverse transcriptase.

27. The composition of claim 16, wherein said reverse transcriptase is an AMV reverse transcriptase or a RSV reverse transcriptase.

28. The composition of claim 16, wherein said polymerase is an RNA polymerase or a DNA polymerase.

29. The composition of claim 28, wherein said DNA polymerase is thermostable.

30. A kit comprising an enzyme selected from the group consisting of a pentosyltransferase, a phosphotransferase with an alcohol group as acceptor, a nucleotidyltransferase, and a carboxy-lyase, a substrate which is capable of either accepting a phosphate radical to give a phosphorylated product from pyrophosphate or effecting transfer of pyrophosphate when in the presence of said enzyme; and
   at least one polymerase or at least one reverse transcriptase.

31. The kit of claim 30, wherein said reverse transcriptase is a retroviral reverse transcriptase.

32. The kit of claim 30, wherein said reverse transcriptase is an AMV reverse transcriptase or a RSV reverse transcriptase.

33. The kit of claim 30, wherein said polymerase is an RNA polymerase or a DNA polymerase.

34. The kit of claim 33, wherein said DNA polymerase is thermostable.

* * * * *